(12) United States Patent
Yanagita et al.

(10) Patent No.: US 7,902,112 B2
(45) Date of Patent: Mar. 8, 2011

(54) FLUIDIZED BED CATALYST FOR PRODUCING ACRYLONITRILE AND PROCESS FOR PRODUCING ACRYLONITRILE

(75) Inventors: Motoo Yanagita, Yokohama (JP); Kenichi Miyaki, Yokohama (JP); Hirokazu Watanabe, Yokohama (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 139 days.

(21) Appl. No.: 12/446,759

(22) PCT Filed: Oct. 23, 2007

(86) PCT No.: PCT/JP2007/070653
§ 371 (c)(1),
(2), (4) Date: Apr. 23, 2009

(87) PCT Pub. No.: WO2008/050767
PCT Pub. Date: May 2, 2008

(65) Prior Publication Data
US 2009/0270648 A1    Oct. 29, 2009

(30) Foreign Application Priority Data
Oct. 26, 2006   (JP) .................................. 2006-291087

(51) Int. Cl.
*B01J 21/08* (2006.01)
*C07C 255/08* (2006.01)

(52) U.S. Cl. ......... 502/241; 502/242; 502/243; 502/249; 502/251; 502/255; 558/462

(58) Field of Classification Search .................. None
See application file for complete search history.

(56) References Cited

U.S. PATENT DOCUMENTS

| | | | |
|---|---|---|---|
| 3,882,159 A | 5/1975 | Callahan et al. | |
| 4,536,483 A | 8/1985 | Sasaki et al. | |
| 5,212,137 A | 5/1993 | Suresh et al. | |
| 5,688,739 A | 11/1997 | Drenski et al. | |
| 5,834,394 A | 11/1998 | Chen et al. | |
| 5,840,648 A | 11/1998 | Suresh et al. | |
| 6,084,119 A | 7/2000 | Midorikawa et al. | |
| 6,420,307 B1 | 7/2002 | Wu et al. | |
| 6,458,742 B1 | 10/2002 | Paparizos et al. | |
| 6,642,405 B1 | 11/2003 | Mori et al. | |
| 6,653,496 B1 | 11/2003 | Mori et al. | |
| 7,365,041 B2 | 4/2008 | Miyaki et al. | |
| 2002/0198398 A1 | 12/2002 | Paparizos et al. | |
| 2004/0106817 A1 | 6/2004 | Paparizos et al. | |
| 2004/0248734 A1 | 12/2004 | Miyaki et al. | |
| 2005/0140820 A1 | 6/2005 | Takeuchi et al. | |
| 2006/0194693 A1 | 8/2006 | Watanabe et al. | |

FOREIGN PATENT DOCUMENTS

| | | |
|---|---|---|
| JP | 58 57422 | 12/1983 |
| JP | 33 11 521 | 1/1984 |
| JP | 59 193136 | 11/1984 |
| JP | 2 56938 | 12/1990 |
| JP | 7 303836 | 11/1995 |
| JP | 10 43595 | 2/1998 |
| JP | 11 169715 | 6/1999 |
| JP | 2001 114740 | 4/2001 |
| JP | 2001 187771 | 7/2001 |
| JP | 3214975 | 10/2001 |
| JP | 2003 507180 | 2/2003 |
| JP | 2003 117397 | 4/2003 |
| JP | 2004 505766 | 2/2004 |
| JP | 3534431 | 6/2004 |
| JP | 2006 507937 | 3/2006 |
| WO | 97 33863 | 9/1997 |

OTHER PUBLICATIONS

U.S. Appl. No. 12/398,619, filed Mar. 5, 2009, Miyaki, et al.
U.S. Appl. No. 12/393,494, filed Feb. 26, 2009, Watanabe, et al.

*Primary Examiner* — Kamal A Saeed
(74) *Attorney, Agent, or Firm* — Oblon, Spivak, McClelland, Maier & Neustadt, L.L.P.

(57) ABSTRACT

A fluidized bed catalyst for producing acrylonitrile capable of maintaining a high yield of acrylonitrile over a long time, and a process for producing acrylonitrile using the catalyst are provided. A fluidized bed catalyst for producing acrylonitrile having a composition represented by a following general formula:

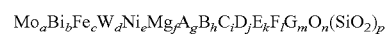

$$Mo_aBi_bFe_cW_dNi_eMg_fA_gB_hC_iD_jE_kF_lG_mO_n(SiO_2)_p$$

In the formula, A represents Ce and La, B represents Ca, Sr, Ba, Mn, Co, Cu, Zn and Cd, C represents Y, Pr, Nd, Sm, Al, Cr, Ga and In, D represents Ti, Zr, V, Nb, Ta, Ge, Sn, Pb and Sb, E represents Ru, Rh, Pd, Re, Os, Ir, Pt and Ag, F represents P, B and Te, G represents Li, Na, K, Rb, Cs and Tl, $SiO_2$ represents silica, when a=10, b=0.1 to 1.5, c=0.5 to 3, d=0.1 to 1.5, e=0.1 to 8, f=0.1 to 5, g=0.1 to 1.5, h=0 to 8, i=0 to 3, j=0 to 3, k=0 to 3, l=0 to 3, m=0.01 to 2, p=10 to 200 and n is the atomic ratio of oxygen required to satisfy the valence of each of the elements excluding silicon, and $(a\times2+d\times2)/(b\times3+c\times3+e\times2+f\times2+g\times3+h\times2+i\times3+m\times1)=0.90$ to 1.00).

2 Claims, No Drawings

FLUIDIZED BED CATALYST FOR PRODUCING ACRYLONITRILE AND PROCESS FOR PRODUCING ACRYLONITRILE

TECHNICAL FIELD

The present invention relates to a fluidized bed catalyst for producing acrylonitrile by vapor phase ammoxidation of propylene by molecular oxygen and ammonia, and to a process for producing acrylonitrile using the catalyst.

The present application claims priority based on Japanese Patent Application No. 2006-291087, filed in Japan on Oct. 26, 2006, the content of which is incorporated herein by reference.

BACKGROUND ART

Numerous proposals have been made regarding a fluidized bed catalyst for producing acrylonitrile by vapor phase ammoxidation of propylene by molecular oxygen and ammonia. For example, fluidized bed catalysts containing molybdenum have been disclosed having as main components thereof molybdenum, bismuth and iron, and which are further compounded with various metal components (Patent Documents 1 to 10).

In addition, a process for regenerating a catalyst of low activity by adding molybdenum-containing substances to a catalyst layer during ammoxidation reaction (hereinafter, simply referred to as a reaction) in a process for producing acrylonitrile by vapor phase ammoxidation with a catalyst including molybdenum; and a process to maintain the performance of a catalyst for a long time by adding molybdenum-containing substances in addition to a catalyst including molybdenum in the catalyst before the start of the reaction have been proposed (Patent Documents 11 to 15).

However, molybdenum vaporizes from a catalyst and molybdenum-containing substances, and is deposited on cooling instruments such as a cooling coil of the fluidized bed reactor in a process to regenerate a catalyst of low activity by adding molybdenum-containing substances to the catalyst during ammoxidation in a conventional process for producing acrylonitrile by vapor phase ammoxidation with a catalyst including molybdenum, and in a process to maintain the performance of a catalyst for a long time by adding molybdenum-containing substances in addition to a catalyst including molybdenum in the catalyst before the start of the reaction. If the molybdenum is deposited on cooling instruments, there are cases in which it becomes difficult to stably operate the fluidized bed reactor for a long time due to heat transfer inhibition.

Therefore, in order to stably produce acrylonitrile for a long time, it is desirable to reduce the amount of molybdenum-containing substances added, and in order to accomplish this, it is desirable to develop a catalyst for producing acrylonitrile capable of maintaining stable yield of acrylonitrile for a long time using as small an added amount of molybdenum-containing substances as possible.

In addition, a fluidized bed reactor can be stably operated with conventional catalysts for a long time without such problems described above. However, these catalysts are not industrially suitable due to low yield production of acrylonitrile. Therefore, development of a catalyst for producing acrylonitrile stably for a long time and also at high yield has been desired.

[Patent Document 1] U.S. Pat. No. 5,212,137
[Patent Document 2] U.S. Pat. No. 5,688,739
[Patent Document 3] U.S. Pat. No. 5,834,394
[Patent Document 4] Japanese Patent No. 3214975
[Patent Document 5] Japanese Patent No. 3534431
[Patent Document 6] US Patent Application No. 2004/0106817
[Patent Document 7] Japanese Unexamined Patent Application, First Publication No. Hei 10-043595
[Patent Document 8] Japanese Laid-Open Patent Application No. 2001-114740
[Patent Document 9] Japanese Laid-Open Patent Application No. 2001-187771
[Patent Document 10] Japanese Laid-Open Patent Application No. 2003-117397
[Patent Document 11] Japanese Examined Patent Application, Second Publication No. Sho 58-57422
[Patent Document 12] Japanese Unexamined Patent Application, First Publication No. Sho 59-193136
[Patent Document 13] German Patent Application No. 3311521
[Patent Document 14] Japanese Examined Patent Application, Second Publication No. Hei 2-56938
[Patent Document 15] International Publication WO No. 97/33863 pamphlet

DISCLOSURE OF THE INVENTION

Problems to be Solved by the Invention

An object of the present invention is to provide a catalyst for producing acrylonitrile capable of maintaining a high acrylonitrile yield for a long time using as small an added amount of molybdenum-containing substances as possible, and to provide a process for producing acrylonitrile enabling stable production of acrylonitrile on an industrial scale at a high acrylonitrile yield.

Means for Solving the Problems

As a result of conducting extensive studies on a catalyst for producing acrylonitrile containing molybdenum, bismuth, and iron, the inventors of the present invention found that by further compounding these components with specific metals at specific ratios, a catalyst maintaining a high acrylonitrile yield can be obtained even if the additive amount of the molybdenum-containing substances are reduced, thereby leading to completion of the present invention.

In other words, the fluidized bed catalyst for producing acrylonitrile (hereafter, simply referred to as a catalyst of the present invention) is characterized by having the composition represented by the following general formula:

$$Mo_aBi_bFe_cW_dNi_eMg_fA_gB_hC_iD_jE_kF_lG_mO_n(SiO_2)_p$$

In the formula, Mo represents molybdenum, Bi represents bismuth, Fe represents iron, W represents tungsten, Ni represents nickel, Mg represents magnesium, O represents oxygen, component A represents at least one element selected from the group consisting of cerium and lanthanum, component B represents at least one element selected from the group consisting of calcium, strontium, barium, manganese, cobalt, copper, zinc and cadmium, component C represents at least one element selected from the group consisting of yttrium, praseodymium, neodymium, samarium, aluminum, chromium, gallium and indium, component D represents at least one element selected from the group consisting of titanium, zirconium, vanadium, niobium, tantalum, germanium, tin, lead and antimony, component E represents at least one element selected from the group consisting of ruthenium, rhodium, palladium, rhenium, osmium, iridium, platinum and silver, component F represents at least one element selected from the group consisting of phosphorus, boron and tellurium, component G represents at least one element selected from the group consisting of lithium, sodium, potassium, rubidium, cesium and thallium, $SiO_2$ represents silica, a, b, c, d, e, f, g, h, i, j, k, l, m, n and p represent the atomic ratio of each element (silicon in the case of silica), when a=10, b=0.1 to 1.5, c=0.5 to 3, d=0.1 to 1.5, e=0.1 to 8, f=0.1 to 5, g=0.1 to 1.5, h=0 to 8, i=0 to 3, j=0 to 3, k=0 to 3, l=0 to 3, m=0.01 to 2, p=10 to 200 and n is the atomic ratio of oxygen required to satisfy the valence of each of the elements excluding silicon, and (a×2+d×2)/(b×3+c×3+e×2+f×2+g×3+h×2+i×3+m×1)=0.90 to 1.00.

A process for producing acrylonitrile of the present invention includes an acrylonitrile production by reacting propylene, molecular oxygen and ammonia in the presence of a catalyst in the fluidized bed reactor having a cooling instrument, with use of the catalyst of the present invention.

Effects of the Invention

According to the catalyst for producing acrylonitrile of the present invention, a high yield of acrylonitrile can be maintained for a long time with as small added amount of molybdenum-containing substances as possible. Due to the above, the additive amount of the molybdenum-containing substances can be reduced. As a result, the amount of vaporized molybdenum becomes small resulting in deposits on the cooling instruments of the fluidized bed reactor being decreased, and acrylonitrile can be stably produced on an industrial scale over a long time.

BEST MODE FOR CARRYING OUT THE INVENTION

The catalyst of the present invention is the fluidized bed catalyst consisting of composite oxide and the composition is represented by the following general formula:

$$Mo_aBi_bFe_cW_dNi_eMg_fA_gB_hC_iD_jE_kF_lG_mO_n(SiO_2)_p$$

In the formula, Mo represents molybdenum, Bi represents bismuth, Fe represents iron, W represents tungsten, Ni represents nickel, Mg represents magnesium, O represents oxygen, A represents at least one element selected from the group consisting cerium and lanthanum, B represents at least one element selected from the group consisting calcium, strontium, barium, manganese, cobalt, copper, zinc and cadmium, C represents at least one element selected from the group consisting yttrium, praseodymium, neodymium, samarium, aluminum, chromium, gallium and indium, D represents at least one element selected from the group consisting titanium, zirconium, vanadium, niobium, tantalum, germanium, tin, lead and antimony, E represents at least one element selected from the group consisting ruthenium, rhodium, palladium, rhenium, osmium, iridium, platinum and silver, F represents at least one element selected from the group consisting phosphorus, boron and tellurium, G represents at least one element selected from the group consisting lithium, sodium, potassium, rubidium, caesium and thallium, and $SiO_2$ represents silica.

In addition, in the formula, a, b, c, d, e, f, g, h, i, j, k, l, m, n and p represent the atomic ratio of each element (silicon in the case of silica), when a=10, b=0.1 to 1.5 and preferably 0.2 to 1.2, c=0.5 to 3 and preferably 0.6 to 2.5, d=0.1 to 1.5 and preferably 0.2 to 1.2, e=0.1 to 8 and preferably 0.2 to 7, f=0.1 to 5 and preferably 0.2 to 4, g=0.1 to 1.5 and preferably 0.2 to 1.2, h=0 to 8 and preferably 0 to 6, i=0 to 3 and preferably 0 to 2, j=0 to 3 and preferably 0 to 2, k=0 to 3 and preferably 0 to 2, l=0 to 3 and preferably 0 to 2, m=0.01 to 2 and preferably 0.05 to 1.5, p=10 to 200 and n is the atomic ratio of oxygen required to satisfy the valence of each of the elements excluding silicon.

In addition, in the catalyst of the present invention, when a=10, X/Y represented by the following equation is 0.90 to 1.00 and preferably 0.92 to 0.99.

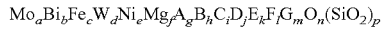

$$X/Y=(a\times2+d\times2)/(b\times3+c\times3+e\times2+f\times2+g\times3+h\times2+i\times3+m\times1)$$

X is the sum of the product of the valence of molybdenum as molybdic acid (2) and the atomic ratio (a) of molybdenum, and the product of the valence of tungsten as tungstic acid (2) and the atomic ratio (d) of tungsten.

Y is the sum of the product of the valence (3) and the atomic ratio (b) of bismuth, the product of the valence (3) and the atomic ratio (c) of iron, the product of the valence (2) and the atomic ratio (e) of nickel, the product of the valence (2) and the atomic ratio (f) of magnesium, the product of the valence (3) and the atomic ratio (g) of component A, the product of the valence (2) and the atomic ratio (h) of component B, the product of the valence (3) and the atomic ratio (i) of component C and the product of the valence (1) and the atomic ratio (m) of component G.

Molybdenum, bismuth, iron, tungsten, nickel, magnesium, component A, component G and silica are essential components, and the object of the present invention cannot be achieved unless each is within the composition range of the aforementioned general formula. It is particularly important in the present invention that during production of a catalyst having molybdenum and tungsten as essential components thereof, a metal element capable of forming a salt with molybdic acid and tungstic acid (bismuth, iron, nickel, magnesium, component A, component B, component C and component G) be added in a suitable amount.

In other words, when the value of X/Y is less than 0.90, there is a surplus of the metal element serving as counter ions of the molybdic acid and tungstic acid in the production of the catalyst. The excess metal element ends up becoming an oxide and the like without forming a molybdate and a tungstate. As a result, the selectivity of acrylonitrile decreases during production of acrylonitrile using the resulting catalyst.

In contrast, when the value of X/Y is greater than 1.00, there is a shortage of the metal element serving as counter ions of the molybdic acid and tungstic acid, the molybdenum and tungsten end up being in excess in the catalyst. As a result, the selectivity of acrylonitrile decreases during production of acrylonitrile using the resulting catalyst. In addition, the amount of vaporized molybdenum becomes excessively large resulting in increased deposits of molybdenum on the cooling coil and the like used as a cooling instrument of the fluidized bed reactor.

In addition, crystal structure of the catalyst stabilizes and the selectivity of acrylonitrile which varies with the changes of the crystal structure of the catalyst may be suppressed by combining a divalent metal such as nickel or magnesium.

Also, in the catalyst of the present invention, when the sum of the atomic ratio of bismuth and the atomic ratio of compound A (b+g) is smaller than the atomic ratio c of iron, an object of the present invention will be particularly finely achieved.

In the present invention, the composition of the catalyst for producing acrylonitrile refers to the bulk composition of the catalyst, and provided that remarkably highly volatile components are not used, the catalyst composition (atomic ratio) may be calculated from the charged amounts of the raw materials of each element that composes the catalyst.

The shape of the catalyst of the present invention is preferably spherical. In addition, the outer diameter thereof is preferably within the range of 1 to 200 μm and particularly preferably within the range of 5 to 100 μm.

The method for preparing the catalyst of the present invention preferably consists of formulating an aqueous slurry containing raw materials of each element that composes the catalyst, drying the resulting aqueous slurry, and calcining the resulting dried product at a temperature of 500 to 750° C. All of elements desired to compose the catalyst are preferably contained in the aqueous slurry at the desired atomic ratios thereof. In the case all elements desired to compose the catalyst are not contained at the desired atomic ratios thereof, the resulting catalyst may be impregnated with elements not present in adequate amounts.

Examples of raw materials of each element include oxides of each element or nitrates, ammonium salts, hydroxides and the like that can be easily converted to oxides.

Examples of raw materials of the molybdenum component include ammonium paramolybdate, ammonium dimolybdate, molybdenum trioxide, molybdenum dioxide, molybdic acid, molybdenum chloride and the like.

Examples of raw materials of the bismuth component include bismuth oxide, bismuth nitrate, bismuth carbonate, bismuth subcarbonate and the like.

Examples of raw materials of the iron component include iron (III) nitrate, iron (III) oxide, ferrosoferric oxide, iron (II) chloride, iron (III) chloride and the like. In addition, metallic iron may be used with dissolving in nitric acid and the like.

Examples of raw materials of the tungsten component include ammonium paratungstate, ammonium metatungstate, tungsten trioxide and the like.

Examples of raw materials of the nickel component include nickel nitrate, nickel oxide (II), nickel hydroxide, nickel chloride and the like.

Examples of raw materials of the magnesium component include magnesium nitrate, magnesium oxide, magnesium hydroxide, magnesium chloride and the like.

Examples of raw materials of the cerium component include cerium nitrate (III), cerium oxide (IV), cerium carbonate (III) and cerium chloride (III) and the like.

Examples of raw materials of the lanthanum component include lanthanum nitrate, lanthanum oxide, lanthanum carbonate and lanthanum chloride and the like.

Examples of raw materials of other elements include nitrates, carbonates, acetates, ammonium salts, oxides, hydroxides, halides and the like of each element.

A plurality of raw materials of each element may also be combined.

Colloidal silica is preferable for the silica raw material. The colloidal silica may be suitably selected from commercially available products. The average particle size of colloidal particles in the colloidal silica is preferably 2 to 100 nm and particularly preferably 5 to 80 nm. In addition, the colloidal silica may be that in which the particle size distribution of colloidal particles has a single peak or that in which the particle size distribution of colloidal particles is consist of multiple peaks.

For drying the aqueous slurry, spray dryer is preferably used, particularly a rotating disk-type spray dryer, a pressure nozzle-type spray dryer or two-fluid nozzle-type spray dryer and the like since a spherical shape is preferable for the shape of the resulting dried product and adjustment of particle diameter is comparatively easy.

A desirable catalyst active structure is formed by calcining the resulting dried product at a temperature within the range of 500 to 750° C. Since a satisfactory catalyst is not obtained if the calcining time is too short, the calcining time is preferably 1 hour or more, and since extraordinary effects are not obtained even if calcining time is extended beyond the required calcining time, the calcining time is normally 20 hours or less. A method using a general-purpose calcining furnace can be used for the calcining method without any particular limitations. The calcining furnace is preferably a rotary kiln or fluidized bed calciner and the like.

During calcining, although the dried product may be immediately calcined at a temperature within the range of 500 to 750° C., calcining is more preferably carried out by preliminarily calcining in one to two stages at a temperature of 250 to 400° C. and/or 400 to 490° C. followed by calcining at a temperature within the range of 500 to 750° C.

When producing acrylonitrile by vapor phase ammoxidation of propylene by molecular oxygen (to simply be referred to as oxygen) and ammonia using the catalyst of the present invention, a fluidized bed reactor having cooling instruments is used.

Examples of a cooling instrument include a cooling coil, a cooling pipe and a heat exchanger.

When vapor phase ammoxidation is carried out, air is industrially advantageous as the oxygen source. Oxygen-enriched air may also be used by adding pure oxygen as necessary as the oxygen source.

The concentration of propylene in the raw material gas can be varied over a wide range, is suitably 1 to 20% by volume and particularly preferably 3 to 15% by volume. The molar ratio of propylene to oxygen in the raw material gas (propylene:oxygen) is preferably 1:1.5 to 1:3. In addition, the molar ratio of propylene to ammonia in the reaction gas (propylene:ammonia) is preferably 1:1 to 1:1.5.

The raw material gas may be diluted with an inert gas or water vapor and the like.

The reaction pressure when carrying out vapor phase ammoxidation is preferably from atmospheric pressure to 500 kPa.

The reaction temperature when carrying out vapor phase ammoxidation is preferably within the range of 400 to 500° C.

The additive amount of the molybdenum-containing substances when carrying out vapor phase ammoxidation is not particularly limited as long as the performance of the catalyst is maintained for a long time. However, the molybdenum which is included in the molybdenum-containing substances is preferably 0.001 to 0.5% by mass relative to the catalyst filled in the fluidized bed reactor for each adding the molybdenum-containing substances, and more preferably 0.005 to 0.2% by mass. If the amount of molybdenum is too small, recovery of acrylonitrile yield might not be observed. If the amount of molybdenum is too large, the improvement to the acrylonitrile yield would be reduced because the combustion of ammonia increases. In addition, stable vapor phase ammoxidation for a long time would be difficult because molybdenum evaporated from the molybdenum-containing substances added when carrying out the vapor phase ammoxidation adheres to the cooling coil and the like inside the fluidized bed reactor.

In addition, such an amount of molybdenum is preferably added more than once in 1 to 30 days, and more preferably added more than once in 1 to 7 days.

Also, the time to add the molybdenum-containing substances to the catalyst filled in the fluidized bed reactor may be before the reaction starts. In other words, molybdenum-containing substances as well as the catalyst of the present invention may be added to the catalyst filled in the fluidized bed reactor before carrying out ammoxidation.

The molybdenum-containing substances to be added when carrying out vapor phase ammoxidation is not particularly limited. However, molybdenum trioxide, molybdic acid, ammonium dimolybdate and ammonium paramolybdate are preferably used.

EXAMPLES

Example

Effects of the present invention are indicated through the following examples. The term "parts" in the following examples and comparative examples refers to parts by mass.

Tests of catalyst activity were carried out according to the procedure described below.

(1) Activity Test of Catalysts:

Production of acrylonitrile by ammoxidation of propylene was carried out using a fluidized bed reactor having an inner diameter of 43 mm and length of 1 m.

At that time, a mixed gas of propylene, ammonia, air and water vapor at a molar ratio of 1/1.2/9.5/0.5 was introduced into the reactor at a gas linear velocity of 8 cm/sec, the reaction temperature was set to 440° C. and the reaction pressure was set to 200 kPa. In addition, an analysis of the reactive test was carried out at a frequency of one or more times per 100 hours, and the amount of catalyst was suitably adjusted so that the propylene conversion rate was 98.0 to 98.2%.

In addition, as a cooling coil, a U-shaped carbon steel pipe having an inner diameter of 2 mm and length of 150 mm was installed in the reactor and air (room temperature) was introduced into the coil at 1 Nm³/hour during the production of an acrylonitrile. Furthermore, during production of acrylonitrile, 0.02% by mass of molybdenum relative to the mass of the catalyst filled in the reactor was added at the rate of once a week in the form of ammonium paramolybdate.

The analyses of the reactive test were carried out by gas chromatography.

In addition, propylene conversion rate, acrylonitrile selectivity and acrylonitrile yield were defined in the manner indicated below.

Propylene conversion rate (%)=Q/P×100
Acrylonitrile selectivity (%)=R/Q×100
Acrylonitrile yield (%)=R/P×100

Here, P represents the number of moles of propylene supplied to the reaction, Q represents the number of moles of propylene that reacted and R represents the number of moles of acrylonitrile formed.

Example 1

A solution of 1968.9 parts of ammonium paramolybdate dissolved in 4000 parts of water was added to 7816.7 parts of 30% by mass silica sol while stirring followed by heating to 45° C. (Liquid A).

Separate from the above, 324.6 parts of bismuth nitrate were dissolved in 2000 parts of 17% by mass nitric acid while stirring followed by the sequential addition of 675.8 parts of iron (III) nitrate, 1459.3 parts of nickel nitrate, 285.9 parts of magnesium nitrate, 290.5 parts of cerium nitrate, 162.3 parts of cobalt nitrate, 223.1 parts of chromium nitrate, 7.9 parts of potassium nitrate and 13.2 parts of rubidium nitrate to this solution followed by heating to 45° C. (Liquid B).

After adding Liquid B to Liquid A while stirring, 258.5 parts of a 50% aqueous solution of ammonium metatungstate (50% by mass as $WO_3$) heated to 45° C. were added thereto to obtain a slurry.

The resulting slurry was dried with a rotating disk-type spray dryer while controlling the temperature at the hot air inlet to 280° C. and the temperature at the outlet to 150° C.

After preliminarily calcining the dried product for 2 hours at 300° C. and then for 2 hours at 440° C., the product was calcined in a fluidized bed calciner for 3 hours at 600° C. to obtain a catalyst 1.

The composition of the catalyst 1 obtained in this manner was calculated from the charged amounts of the raw materials as indicated below.

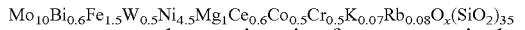

$Mo_{10}Bi_{0.6}Fe_{1.5}W_{0.5}Ni_{4.5}Mg_1Ce_{0.6}Co_{0.5}Cr_{0.5}K_{0.07}Rb_{0.08}O_x(SiO_2)_{35}$

Here, x represents the atomic ratio of oxygen required to satisfy the valence of each of the other elements (excluding silicon).

When the resulting catalyst 1 was tested for activity under the conditions indicated in (1) above, the acrylonitrile yield progressed favorably, demonstrating a value of 82.2% at 50 hours after the start of the reaction, 82.5% at 500 hours after the start of the reaction and 82.6% at 1000 hours after the start of the reaction. The results are shown in Table 3.

Examples 2 to 6, Comparative Examples 1 to 5

A catalyst having the composition shown in Table 1 and Table 2 was produced in the same manner as Example 1. In other words, the catalyst was produced in the same manner as Example 1 after preparing the charged amounts of the raw materials of each element according to the desired catalyst compositions. However raw materials of the nitrate including lanthanum (La), zinc (Zn), manganese (Mn), germanium (Ge), palladium (Pd), ruthenium (Ru) and caesium (Cs), raw materials of the anhydrous borate including boron (B) and raw materials of the 85% by mass phosphoric acid including phosphorus (P) were used. In addition, calcining conditions were changed to the conditions shown in Table 3.

A catalyst activity test was performed in the same manner as Example 1 in each resulting catalyst. The results are shown in Table 3.

Example 7

A solution of 1944.5 parts of ammonium paramolybdate dissolved in 4000 parts of water was added to 7720.0 parts of 30% by mass silica sol while stirring followed by heating to 45° C. (Liquid A).

Separate from the above, 427.5 parts of bismuth nitrate were dissolved in 2000 parts of 17% by mass nitric acid while stirring followed by the sequential addition of 519.1 parts of iron (III) nitrate, 1345.1 parts of nickel nitrate, 564.8 parts of magnesium nitrate, 238.5 parts of lanthanum nitrate, 96.2 parts of cobalt nitrate, 14.6 parts of niobium oxide, 7.8 parts of potassium nitrate and 13.0 parts of rubidium nitrate to this solution followed by heating to 45° C. (Liquid B).

In addition, a solution of 143.8 parts of ammonium paratungstate dissolved in 800 parts of water followed by heating to 60° C. 148.3 parts of iron (III) nitrate were dissolved in 100 parts of water while stirring (Liquid C).

After adding Liquid B to Liquid A while stirring, Liquid C was added thereto to obtain a slurry.

The resulting slurry was dried with a rotating disk-type spray dryer while controlling the temperature at the hot air inlet to 280° C. and the temperature at the outlet to 150° C.

After preliminarily calcining the dried product for 2 hours at 300° C. and then for 2 hours at 440° C., the product was calcined in a fluidized bed calciner for 3 hours at 600° C. to obtain a catalyst 7.

The composition of the catalyst 7 obtained in this manner was calculated from the charged amounts of the raw materials as indicated below.

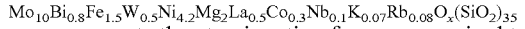

$Mo_{10}Bi_{0.8}Fe_{1.5}W_{0.5}Ni_{4.2}Mg_2La_{0.5}Co_{0.3}Nb_{0.1}K_{0.07}Rb_{0.08}O_x(SiO_2)_{35}$

Here, x represents the atomic ratio of oxygen required to satisfy the valence of each of the other elements (excluding silicon).

When the resulting catalyst 7 was tested for activity under the conditions indicated in (1) above, the acrylonitrile yield progressed favorably, demonstrating a value of 82.2% at 50 hours after the start of the reaction, 82.4% at 500 hours after the start of the reaction and 82.4% at 1000 hours after the start of the reaction. The results are shown in Table 3.

Example 8 and 9

A catalyst having the composition shown in Table 1 was produced in the same manner as Example 7. In other words, a catalyst was produced in the same manner as Example 7 after preparing the charged amounts of the raw materials of each element according to the desired catalyst compositions. However, raw materials of the nitrate including cerium (Ce), manganese (Mn), chromium (Cr), neodymium (Nd), samarium (Sm) and zirconium (Zr), raw materials of the ammonium metavanadate including vanadium (V) and raw materials of the telluric acid including tellurium (Te) were used. In addition, calcining conditions were changed to the conditions shown in Table 3.

A catalyst activity test was performed in the same manner as Example 7 in each resulting catalyst. The results are shown in Table 3.

Acrylonitrile yield at 1000 hours after the start of the reaction compared to 500 hours after the start of the reaction was in a range of −0.7% to −0.5% in the Comparative Examples 1 to 5 compared to in a range of −0.2% to 0.4% in the Examples 1 to 9.

Example 10

A solution of 1777.9 parts of ammonium paramolybdate dissolved in 4000 parts of water was added to 8067.0 parts of 30% by mass silica sol while stirring followed by heating to 45° C. (Liquid A).

Separate from the above, 293.1 parts of bismuth nitrate were dissolved in 2000 parts of 17% by mass nitric acid while stirring followed by the sequential addition of 610.3 parts of iron (III) nitrate, 466.9 parts of a 50% aqueous solution of ammonium metatungstate (50% by mass as $WO_3$), 878.5 parts of nickel nitrate, 129.1 parts of magnesium nitrate, 174.9 parts of cerium nitrate, 439.6 parts of cobalt nitrate, 144.5 parts of manganese nitrate, 604.5 parts of chromium nitrate, 87.6 parts of praseodymium nitrate, 15.3 parts of potassium nitrate and 9.8 parts of caesium nitrate to this solution followed by heating to 45° C. (Liquid B).

After adding Liquid B to Liquid A while stirring, a slurry was obtained.

The resulting slurry was dried with a rotating disk-type spray dryer while controlling the temperature at the hot air inlet to 280° C. and the temperature at the outlet to 150° C.

After preliminarily calcining the dried product for 2 hours at 300° C. and then for 2 hours at 440° C., the product was calcined in a fluidized bed calciner for 3 hours at 570° C. to obtain a catalyst 10.

The composition of the catalyst 10 obtained in this manner was calculated from the charged amounts of the raw materials as indicated below.

$$Mo_{10}Bi_{0.6}Fe_{1.5}W_1Ni_3Mg_{0.5}Ce_{0.4}Co_{1.5}Mn_{0.5}Cr_{1.5}Pr_{0.2}K_{0.15}Cs_{0.05}O_x(SiO_2)_{40}$$

Here, x represents the atomic ratio of oxygen required to satisfy the valence of each of the other elements (excluding silicon).

When the resulting catalyst 10 was tested for activity under the conditions indicated in (1) above, the acrylonitrile yield progressed favorably, demonstrating a value of 81.8% at 50 hours after the start of the reaction, 82.2% at 500 hours after the start of the reaction and 82.3% at 1000 hours after the start of the reaction. The results are shown in Table 3.

Comparative Example 6

A catalyst having the composition shown in Table 2 was produced in the same manner as Example 10. In other words, a catalyst was produced in the same manner as Example 10 after preparing the charged amounts of the raw materials of each element according to the desired catalyst compositions. In addition, calcining conditions were changed to those shown in Table 3. This catalyst is different from the catalyst of the present invention with the catalyst which increased the composition ratios of the tungsten in comparison with the catalyst of Example 10.

A catalyst activity test was performed in the same manner as Example 10 in each resulting catalyst. The results are shown in Table 3. This Comparative Example produced an 80.9% acrylonitrile yield at 50 hours after the start of the reaction compared to the 81.8% acrylonitrile yield at 50 hours after the start of the reaction in Example 10. Furthermore, the acrylonitrile yield reduced by 0.1% in this Comparative Example relative to the acrylonitrile yield increased by 0.5% in the Example 10 at 1000 hours after the start of the reaction compared to 50 hours after the start of the reaction.

Comparative Example 7

A catalyst having the composition shown in Table 2 was produced in the same manner as Example 10. In other words, a catalyst was produced in the same manner as Example 10 after preparing the charged amounts of the raw materials of each element according to the desired catalyst compositions. In addition, calcining conditions were changed to the conditions shown in Table 3. This catalyst was different compared to the catalyst of Example 10 in that composition ratio of cerium was 0.

A catalyst activity test was performed in the same manner as Example 10 in each resulting catalyst. The results are shown in Table 3. This comparative example produced an 81.0% acrylonitrile yield at 50 hours after the start of the reaction compared to the 81.8% acrylonitrile yield at 50 hours after the start of the reaction in Example 10. Furthermore, the acrylonitrile yield reduced by 0.3% in this Comparative Example compared to the acrylonitrile yield increased by 0.5% in the example 10 at 1000 hours after the start of the reaction compared to 50 hours after the start of the reaction.

According to the above examples and comparative examples, high yield production of acrylonitrile with a stable yield with the use of the catalyst of the present invention was achieved. In addition, the difference of acrylonitrile yield at 50 hours after the start of the reaction between examples and comparative examples was less than 1%. However, industrially, 250,000 tons of acrylonitrile has been produced per year in large scale plants, even average plants produce approximately 100,000 tons per year. Since 5,000,000-6,000,000 tons of acrylonitrile has been produced per year world-wide, the difference of the acrylonitrile yield can have a significant impact on acrylonitrile production industry. In addition, the difference between acrylonitrile yield at 1000 hours after the start of the reaction compared to 50 hours after the start of the reaction between examples and comparative examples was less than 1%. However, the difference of the acrylonitrile yield can have a significant impact on acrylonitrile production industry because catalysts have been used for several years industrially.

TABLE 1

Catalyst Composition (atomic ratio)

| | | Mo | Bi | Fe | W | Ni | Mg | A | B | C | D | E | F | G | Si | X/Y |
|---|---|---|---|---|---|---|---|---|---|---|---|---|---|---|---|---|
| Examples | 1 | 10 | 0.6 | 1.5 | 0.5 | 4.5 | 1.0 | Ce 0.6 | Co 0.5 | Cr 0.5 | | | | K 0.07 Rb 0.08 | 35 | 0.97 |
| | 2 | 10 | 0.4 | 1.3 | 0.2 | 3.3 | 1.5 | La 0.8 | Zn 0.2 | Cr 1.0 | Ge 0.2 | | B 0.2 | K 0.15 Rb 0.05 | 35 | 0.99 |
| | 3 | 10 | 0.6 | 1.5 | 0.8 | 5.0 | 1.0 | Ce 0.6 | | Cr 0.8 | | | | K 0.15 Rb 0.05 | 35 | 0.95 |
| | 4 | 10 | 0.8 | 1.5 | 0.2 | 4.8 | 1.2 | Ce 0.6 | | | | Pd 0.01 | P 0.1 B 0.1 | K 0.07 Cs 0.08 | 35 | 0.98 |
| | 5 | 10 | 0.6 | 1.3 | 0.5 | 4.7 | 1.0 | Ce 0.9 | Co Mn 0.1 0.2 | Cr 0.5 | | | | K 0.07 Rb 0.08 | 35 | 0.95 |
| | 6 | 10 | 0.6 | 1.5 | 0.5 | 4.5 | 0.5 | Ce 0.5 | Co 1.0 | Cr 0.5 | | Ru 0.05 | P 0.2 | K 0.07 Cs 0.08 | 40 | 0.98 |
| | 7 | 10 | 0.8 | 1.5 | 0.5 | 4.2 | 2.0 | La 0.5 | Co 0.3 | | Nb 0.1 | | | K 0.07 Rb 0.08 | 35 | 0.97 |
| | 8 | 10 | 0.8 | 1.5 | 0.8 | 3.8 | 1.2 | Ce 0.4 | Mn 0.5 | Cr 0.8 Nd 0.2 | Zr 0.2 | | | K 0.15 | 35 | 0.97 |
| | 9 | 10 | 0.5 | 1.8 | 0.5 | 3.5 | 1.5 | Ce 1.0 | | Cr Sm 0.5 0.2 | V 0.1 | | Te 0.2 | K 0.2 | 45 | 0.95 |
| | 10 | 10 | 0.6 | 1.5 | 1.0 | 3.0 | 0.5 | Ce 0.4 | Co Mn 1.5 0.5 | Co Pr 1.5 0.2 | | | | K 0.15 Cs 0.05 | 40 | 0.92 |

TABLE 2

Catalyst Composition (atomic ratio)

| | | Mo | Bi | Fe | W | Ni | Mg | A | B | C | D | E | F | G | Si | X/Y |
|---|---|---|---|---|---|---|---|---|---|---|---|---|---|---|---|---|
| Comparative examples | 1 | 10.5 | 0.6 | 1.5 | | 4.5 | 1.0 | Ce 0.6 | Co 0.5 | Cr 0.5 | | | | K 0.07 Rb 0.08 | 35 | 0.97 |
| | 2 | 10 | 0.6 | 1.5 | | 4.5 | 1.0 | Ce 0.6 | Co 0.5 | Cr 0.5 | | | | K 0.07 Rb 0.08 | 35 | 0.92 |
| | 3 | 9.2 | 0.6 | 1.5 | 0.8 | 5.0 | 1.0 | Ce 0.6 | | Cr 0.8 | | | | K 0.15 Rb 0.05 | 35 | 0.88 |
| | 4 | 10 | 0.6 | 1.5 | 0.8 | 4.2 | 1.0 | Ce 0.6 | | Cr 0.8 | | | | K 0.15 Rb 0.05 | 35 | 1.02 |
| | 5 | 10 | 0.6 | 1.5 | 0.8 | 6.0 | | Ce 0.6 | | Cr 0.8 | | | | K 0.15 Rb 0.05 | 35 | 0.95 |
| | 6 | 10 | 0.6 | 1.5 | 1.7 | 3.0 | 0.5 | Ce 0.4 | Co Mn 1.5 0.5 | Cr Pr 1.5 0.2 | | | | K 0.15 Cs 0.05 | 40 | 0.98 |
| | 7 | 10 | 0.6 | 1.5 | 1.0 | 3.0 | 0.5 | | Co Mn 1.5 0.5 | Cr Pr 1.5 0.2 | | | | K 0.15 Cs 0.05 | 40 | 0.97 |

TABLE 3

| | | Calcining conditions | | Reaction condition | Acrylonitrile yield (%) Elapsed time (hr) | | |
|---|---|---|---|---|---|---|---|
| | | Temperature (°C.) | Time (hr) | Temperature (°C.) | 50 | 500 | 1000 |
| Examples | 1 | 600 | 3 | 440 | 82.2 | 82.5 | 82.6 |
| | 2 | 590 | 3 | 440 | 82.8 | 82.6 | 82.6 |
| | 3 | 590 | 3 | 440 | 82.0 | 82.2 | 82.3 |
| | 4 | 580 | 3 | 440 | 82.7 | 82.5 | 82.5 |
| | 5 | 610 | 3 | 440 | 82.0 | 81.9 | 81.9 |
| | 6 | 580 | 3 | 440 | 82.3 | 82.4 | 82.3 |
| | 7 | 600 | 3 | 440 | 82.5 | 82.4 | 82.4 |
| | 8 | 580 | 3 | 440 | 82.3 | 82.5 | 82.4 |
| | 9 | 610 | 3 | 440 | 82.2 | 82.3 | 82.3 |
| | 10 | 570 | 3 | 440 | 81.8 | 82.2 | 82.3 |
| Comparative examples | 1 | 600 | 3 | 440 | 82.3 | 81.9 | 81.6 |
| | 2 | 600 | 3 | 440 | 82.1 | 81.9 | 81.5 |
| | 3 | 590 | 3 | 440 | 81.5 | 81.3 | 81.0 |
| | 4 | 590 | 3 | 440 | 82.0 | 81.8 | 81.5 |
| | 5 | 590 | 3 | 440 | 82.1 | 81.8 | 81.6 |
| | 6 | 570 | 3 | 440 | 80.9 | 81.0 | 80.8 |
| | 7 | 570 | 3 | 440 | 81.0 | 80.9 | 80.7 |

INDUSTRIAL APPLICABILITY

The catalyst for producing acrylonitrile of the present invention, when producing acrylonitrile by vapor phase ammoxidation of propylene, high yield of acrylonitrile can be maintained for a long time with less additive amount of molybdenum-containing substances compared to the conventional catalyst. As a result, the amount of vaporized molybdenum during the reaction can be reduced, resulting in greatly suppressed deposits of molybdenum on the cooling instruments of the fluidized bed reactor. Since acrylonitrile can be produced stably over a long time with use of the catalyst of the present invention, the acrylonitrile of the present invention has considerable industrial value.

The invention claimed is:

1. A fluidized bed catalyst for producing acrylonitrile comprising a composition represented by a following general formula:

$$Mo_aBi_bFe_cW_dNi_eMg_fA_gB_hC_iD_jE_kF_lG_mO_n(SiO_2)_p$$

wherein, Mo represents molybdenum, Bi represents bismuth, Fe represents iron, W represents tungsten, Ni represents nickel, Mg represents magnesium, O represents oxygen, component A represents at least one element selected from the group consisting of cerium and lanthanum, component B represents at least one element selected from the group consisting of calcium, strontium, barium, manganese, cobalt, copper, zinc and cadmium, component C represents at least one element selected from the group consisting of yttrium, praseodymium, neodymium, samarium, aluminum, chromium, gallium and indium, component D represents at least one element selected from the group consisting of titanium, zirconium, vanadium, niobium, tantalum, germanium, tin, lead and antimony, component E represents at least one element selected from the group consisting of ruthenium, rhodium, palladium, rhenium, osmium, iridium, platinum and silver, component F represents at least one element selected from the group consisting of phosphorus, boron and tellurium, component G represents at least one element selected from the group consisting of lithium, sodium, potassium, rubidium, cesium and thallium, $SiO_2$ represents silica, a, b, c, d, e, f, g, h, i, j, k, l, m, n and p represent the atomic ratio of each element (silicon in the case of silica), where a=10, b=0.1 to 1.5, c=0.5 to 3, d=0.1 to 1.5, e=0.1 to 8, f=0.1 to 5, g=0.1 to 1.5, h=0 to 8, i=0 to 3, j=0 to 3, k=0 to 3, l=0 to 3, m=0.01 to 2, p=10 to 200 and n is the atomic ratio of oxygen required to satisfy the valence of each of the elements excluding silicon, and $(a \times 2 + d \times 2)/(b \times 3 + c \times 3 + e \times 2 + f \times 2 + g \times 3 + h \times 2 + i \times 3 + m \times 1) = 0.90$ to 1.00).

2. A process for producing acrylonitrile, comprising:

reacting propylene, molecular oxygen and ammonia in the presence of a catalyst in the fluidized bed reactor having a cooling instrument;

use of the fluidized bed catalyst for producing acrylonitrile according to claim 1.

* * * * *